United States Patent [19]

Narui et al.

[11] Patent Number: 5,112,816
[45] Date of Patent: May 12, 1992

[54] CORTICORSTEROID-CONTAINING OINTMENTS

[75] Inventors: Takashi Narui, Sakura; Tetsuo Kaneko, Narita; Katsumi Imamori; Akira Iwasa, both of Yotsukaido, all of Japan

[73] Assignee: SS Pharmaceutical Co., Ltd., Tokyo, Japan

[21] Appl. No.: 577,559

[22] Filed: Sep. 5, 1990

[51] Int. Cl.$^5$ .................... A61K 31/57; A61K 31/58; A61K 9/06
[52] U.S. Cl. ..................................... 514/179; 514/969
[58] Field of Search ................. 514/167–182, 514/969

[56] References Cited

U.S. PATENT DOCUMENTS

| | | | |
|---|---|---|---|
| 3,639,434 | 2/1972 | Oxley et al. | 260/397.45 |
| 3,881,000 | 4/1975 | Friedmann et al. | 514/105 |
| 3,906,108 | 9/1975 | Felty | 516/560 |
| 4,124,707 | 11/1978 | Green et al. | 424/241 |
| 4,214,000 | 7/1980 | Papa | 514/787 |
| 4,294,852 | 10/1981 | Wildnauer et al. | 514/179 |
| 4,333,927 | 6/1982 | Ofuchi et al. | 514/179 |
| 4,427,670 | 1/1984 | Ofuchi et al. | 514/969 |
| 4,740,372 | 4/1988 | Boncic | 514/170 |
| 4,865,846 | 9/1989 | Kaufman | 514/912 |
| 4,906,670 | 3/1990 | Higashi et al. | 514/781 |

FOREIGN PATENT DOCUMENTS

0280737 8/1987 European Pat. Off. .

OTHER PUBLICATIONS

Schering C.A. 84:122146g (1976) of FR. Demande 2,555,079, Jul. 18, 1975.
Compernolle et al., (I) C.A. 77:168674m (1972), (II) C.A. 77:393252 (1972).
Dekker et al., C.A. 93:192089a (1980).
Gonzalez et al., C.A. 102:791962 (1985).
Gonzalez et al., C.A. 103:160758b (1985).
STN File Server, File CA, Chemical Abstracts, vol. 77, No. 6, abstract No. 39146s, Columbus, Ohio, U.S.: F. Gstirner et al; "Rheological properties and composition of petrolatum. II", & Arch. Phae. Ber. Deut. Phar. Ges., 305(4), 266–73 (Entire Abstract) (1972).
Takano, Masahiko, Pharmacy Department, Tokyo Teishin Hospital, "Konnichi No Hifu Gaiyozai" (Contemporary External Preparations for the Skin), Article and excerpt translation, p. 546, line 13 to p. 547, line 5, May 15, 1981.

*Primary Examiner*—Shep K. Rose
*Attorney, Agent, or Firm*—Oblon, Spivak, McClelland, Maier & Neustadt

[57] ABSTRACT

Ointments are disclosed, which contain (a) 0.05–1 wt. % of deprodone propionate and (b) 89–99.95 wt. % of a base formed of white petroleum and a liquid hydrocarbon. The ointments may additional contain (c) 1–10 wt. % of a polyhydric alcohol.

9 Claims, 1 Drawing Sheet

CORTICORSTEROID-CONTAINING OINTMENTS

BACKGROUND OF THE INVENTION

1) Field of the Invention

The present invention relates to corticosteroid-containing ointments, and more specifically to corticosteroid-containing ointments which contain deprodone propionate as an effective ingredient, can exhibit its effects to the maximum extent and over a prolonged period of time, do not have skin irritation, and are physicochemically stable.

2) Description of the Related Art

Corticosteroids have heretofore been employed widely as remedial agents in the field of dermatology because they exhibit even in a small amount strong therapeutic effects for inflammatory and allergic skin diseases and have fast-acting property compared with other medicaments.

When a corticosteroid is used as an external preparation for a localized disease in the field of dermatology, it is often applied in the form of an ointment since an ointment has excellent protective and anti-inflammatory action for the skin and gives very little irritation or contact dermatitis to the skin.

The corneum in the surface of the skin however inherently functions as a barrier in order to prevent penetration of foreign substances from the outside into the body. This has led to the problem that sufficient percutaneous absorption cannot be achieved with an ointment containing a steroid ingredient simply mixed in a base which has conventionally been employed in external preparations.

To improve this problem, various percutaneous absorption promoters such as 1-dodecylazacycloheptan-2-one, dimethylsulfoxide and dimethylformamide have been used in recent years. These promoters are however not considered sufficient in safety and feeling of use.

It is also practiced to use a corticosteroid having strong effects so as to tentatively improve the percutaneous absorption or to increase the concentration of a corticosteroid so as to increase the therapeutic effects. These methods are however accompanied by the problem of side effects because the influence to the whole body or a part thereof increases in proportion to the effects and concentration of the corticosteroid.

It has therefore been desired to develop a corticosteroid-containing ointment which has high curative effects and which gives less side effects to the whole body or a part thereof and has higher safety.

It is however to be noted that the curative effects of an ointment significantly vary depending on the kind of its base and the like even when the ointment contains the same effective ingredient at the same concentration and an ointment having excellent curative effects and little side effects can be obtained for the first time when its effective ingredient and its base match well in physicochemical properties.

SUMMARY OF THE INVENTION

Under such circumstances, the present inventors have carried out an extensive investigation on the relationship between individual corticosteroids and bases. As a result, it has been found that addition of deprodone propionate represented by a formula, which is to be described hereinafter, to a specific base can provide an ointment which allows deprodone propionate to exhibit its effects to the maximum extent and over a prolonged period of time, does not have side effects such as skin irritation, and is physicochemically stable, leading to the completion of the present invention.

In one aspect of the present invention, there is thus provided an ointment comprising the following ingredients (a) and (b):

(a) 0.05–1 wt. % of deprodone propionate; and
(b) 89–99.95 wt. % of a base formed of white petrolatum and a liquid hydrocarbon.

The use of white petrolatum as one of components of a base, i.e., component (b) in the present invention makes it possible to cover the skin with an oily film without side effects such as irritation and contact dermatitis to the skin. Therefore, white petrolatum prevents transpiration of water from the skin and permits a sort of ODT (occlusive dressing technique), and further can promote the percutaneous absorption of the medicinal ingredient. In addition, the use of the liquid hydrocarbon significantly improves the spreadability onto the skin, thereby improving the feeling of use, increasing the retention of the medicinal ingredient on the skin and enhancing the curative effects.

The feeling of use can be improved further by the use of a polyhydric alcohol in the present invention.

Corticosteroid-containing ointments according to the present invention remain physicochemically stable even when stored over a long period of time, have substantially no skin irritation and side effects, and exhibit superb curative effects.

DETAILED DESCRIPTION OF THE INVENTION AND PREFERRED EMBODIMENTS

Figure 1:
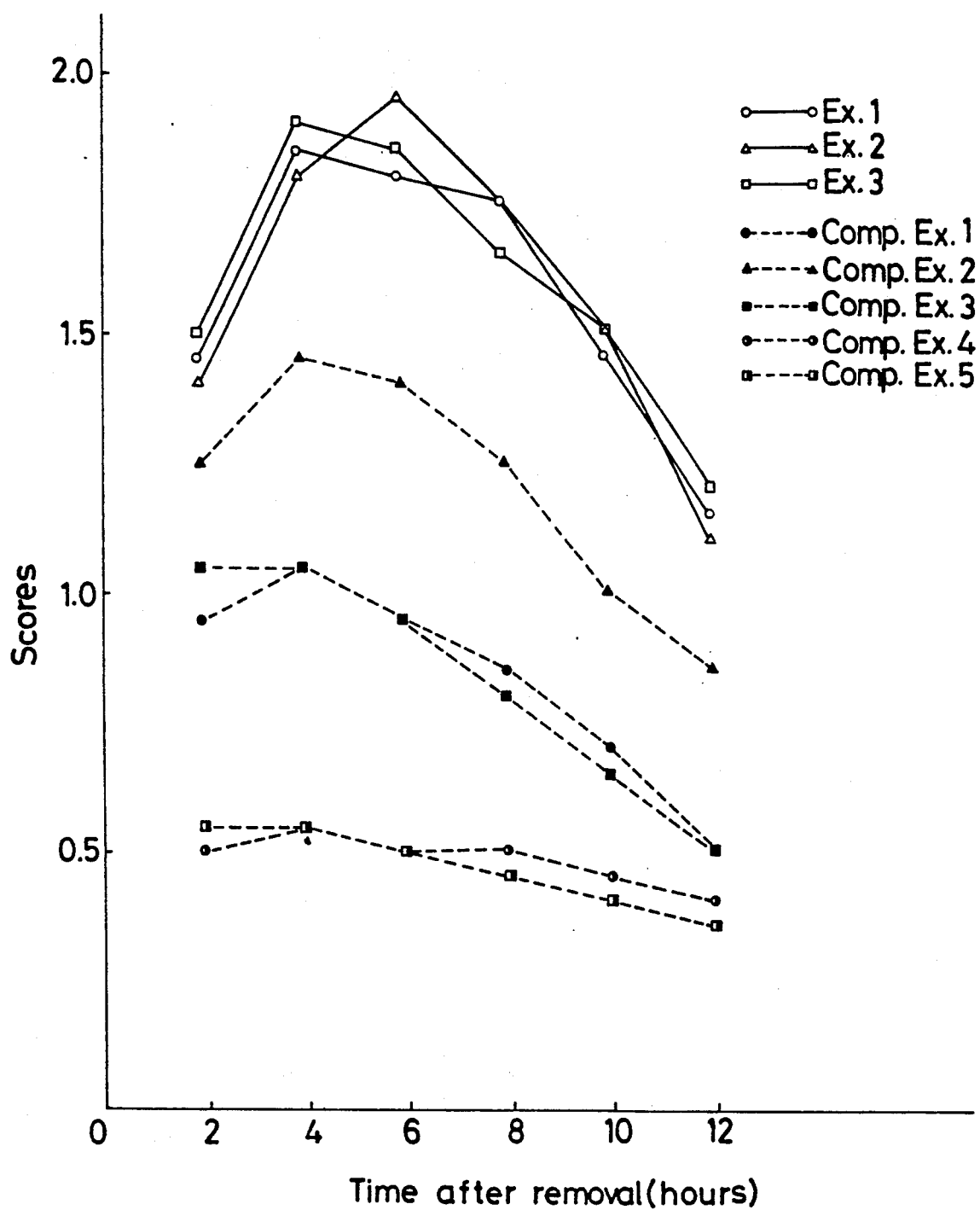
FIG. 1 diagrammatically illustrates the results of a vasoconstriction test of the ointments of Examples 1–3 and Comparative Examples 1–5.

Deprodone propionate, ingredient (a) in the present invention, is a compound which is obtained by esterifying with propionic acid the 17-position of the prednisolone skeleton and deoxidating its 21-position and has the structure represented by the following formula:

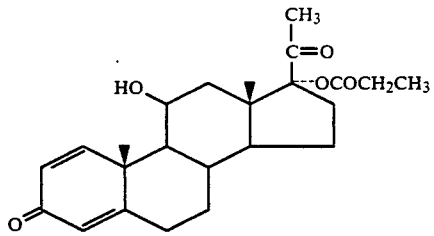

Ingredient (a) is added in an amount of 0.05–1 wt. % (hereinafter indicated merely by "%"), preferably 0.1–0.5%, both based on the whole composition.

The base, ingredient (b), is composed of white petrolatum and a liquid hydrocarbon. Illustrative of the liquid hydrocarbon include light liquid paraffin, liquid paraffin and squalane.

In the present invention, white petrolatum can amount preferably to 74–98.95% of the base, with 85–95% being particularly preferred. The liquid hydrocarbon can account preferably for 1–15%, especially 5-10% of the base. Ingredient (b) is added in an amount of 89-99.95% based on the whole composition.

It is preferred to add a polyhydric alcohol [ingredient (c)] further to the ointment of the present invention Examples of the polyhydric alcohol as ingredient (c) include glycerin, sorbitol, sorbitan and glycols. Among these, it is preferred to use either one of propylene glycol, 1,3-butylene glycol and polyethylene glycols having an average molecular weight of 200-6,000.

Ingredient (c) can be added in an amount of 1-10%, preferably 2-6% based on the whole composition.

It is also preferred to add a stabilizer in the present invention. For example, butylhydroxyanisole, dibutylhydroxytoluene (BHT) or the like can be employed.

The present invention will hereinafter be described in further detail by the following examples, comparative examples and tests.

EXAMPLE 1

| | |
|---|---|
| Deprodone propionate | 0.3 g |
| Light liquid paraffin | 8 g |
| BHT | 0.02 g |
| White petrolatum Sufficient to produce | 100 g |

BHT was melted in light liquid paraffin at 50°-60° C., followed by the dispersion of deprodone propionate. The resultant dispersion was added to white petrolatum which had been heated and melted at 65°-75° C. in advance. After the mixture thus prepared was stirred, it was filtered and then stirred until it became homogeneous. The mixture was cooled to prepare an ointment.

EXAMPLE 2

| | |
|---|---|
| Deprodone propionate | 0.3 g |
| Light liquid paraffin | 5 g |
| Propylene glycol | 5 g |
| BHT | 0.02 g |
| White petrolatum Sufficient to produce | 100 g |

An ointment was prepared in a similar manner to Example 1.

EXAMPLE 3

| | |
|---|---|
| Deprodone propionate | 0.3 g |
| Light liquid paraffin | 5 g |
| 1,3-butylene glycol | 5 g |
| BHT | 0.02 g |
| White petrolatum Sufficient to produce | 100 g |

An ointment was prepared in a similar manner to Example 1.

COMPARATIVE EXAMPLE 1

| | |
|---|---|
| Deprodone propionate | 0.3 g |
| White petrolatum Sufficient to produce | 100 g |

Deprodone propionate was added to white petrolatum which had been heated and melted at 65°-75° C. in advance. After the mixture thus prepared was stirred and filtered, it was stirred until it became homogeneous. The mixture was cooled to room temperature to prepare an ointment.

COMPARATIVE EXAMPLE 2

| | |
|---|---|
| Deprodone propionate | 0.3 g |
| Propylene glycol | 10 g |
| BHT | 0.01 g |
| White petrolatum Sufficient to produce | 100 g |

Deprodone propionate and BHT were added to propylene glycol. The resultant mixture was added to white petrolatum which had been heated and melted at 65°-75° C. in advance. After the mixture thus prepared was stirred and filtered, it was stirred until it became homogeneous. The mixture was cooled to room temperature to prepare an ointment.

COMPARATIVE EXAMPLE 3

| | |
|---|---|
| Deprodone propionate | 0.3 g |
| Propylene glycol | 10 g |
| BHT | 0.02 g |
| Gelled hydrocarbon Sufficient to produce | 100 g |

Deprodone propionate and BHT were added to propylene glycol. The resultant mixture was heated and melted at 50°-60° C. to prepare a trituration and stock melt. Gelled hydrocarbon was added little by little to the melt, whereby gelled hydrocarbon was mixed and dispersed in the melt. An ointment was prepared accordingly.

COMPARATIVE EXAMPLE 4

| | |
|---|---|
| Deprodone propionate | 0.3 g |
| Ethanol | 35 g |
| Carboxyvinyl polymer | 1 g |
| Triethanolamine | 0.8 g |
| BHT | 0.01 g |
| Purified water Sufficient to produce | 100 g |

Deprodone propionate and BHT were dissolved in ethanol in advance. An aqueous solution of carboxyvinyl polymer, said solution having been prepared beforehand as a trituration and stock solution, was added to the ethanol solution, followed by neutralization with triethanolamine. The resultant mixture was diluted with purified water to give the final weight of 100 g, whereby an ointment was prepared.

COMPARATIVE EXAMPLE 5

| | |
|---|---|
| Deprodone propionate | 0.3 g |
| Propylene glycol | 4.2 g |
| Concentrated glycerin | 17.7 g |
| Sorbitol | 3.1 g |
| Light liquid paraffin | 61.0 g |
| Solid paraffin | 3.2 g |
| Propylene glycol monostearate | 0.5 g |
| Sucrose fatty acid ester | 5 g |
| Methyl parahydroxybenzoate | 0.1 g |
| Propyl parahydroxybenzoate | 0.1 g |
| BHT | 0.02 g |
| Purified water Sufficient to produce | 100 g |

Propylene glycol monostearate, sucrose fatty acid ester, methyl parahydroxybenzoate, propyl parahydroxybenzoate and BHT were added under heat and stirring to concentrated glycerin and propylene glycol, followed by the further addition of deprodone propionate. Light liquid paraffin and solid paraffin were added further gradually under stirring. Purified water was then added. After the resultant mixture was stirred, it was cooled to prepare an ointment.

TEST 1

With respect to the ointments obtained in Examples 1–3 and Comparative Examples 1–5, respectively, a vasoconstriction test was conducted on the normal human skin in an open system in accordance with the following testing method.

(Testing method)

An adhesive plaster (30 mm wide, 17 cm long, about 1 mm thick) through which holes having an internal diameter of 10 mm were formed was adhered to a lower middle back area of a volunteer. Each test ointment was applied for 2 hours in two of the holes at a rate of 30 mg per hole. After the two-hour period, the test ointments were removed. After 2, 4, 6, 8, 10 and 12 hours from the removal of the test ointments, the degrees or the presence or absence of skin paleness due to vasoconstriction were determined. Two points were given when marked paleness was observed, one point when apparent paleness was observed, 0.5 point when slight paleness was observed, and 0 point when no paleness was observed. Average of scores on 30 volunteers were determined. The results are diagrammatically shown in FIG. 1.

In the above test, the ointments of Examples 1–3 in which white petrolatum was used as a base and light liquid paraffin was employed in combination with white petrolatum optionally along with one or more of propylene glycol, 1,3-butylene glycol and polyethylene glycol had high averages as shown in FIG. 1. It is hence envisaged that the effects of deprodone propionate were long-lasting.

In addition, bases prepared in accordance with the same formulations as Examples 1–3 and Comparative Examples 1–5 except for the omission of deprodone propionate were applied to lower middle back areas of 30 normal volunteers at two spots per base and volunteer. After 48 hours, the irritation of each base was observed. As is shown in Table 1, irritation (slight erythema) was observed with respect to the bases of Comparative Examples 4 and 5, but similar irritation was practically unobserved with respect to the bases of Examples 1–3.

Regarding physicochemical stability, the ointments of the examples were superior, as shown in Table 2, in discoloration, bleeding and the stability of deprodone propionate to those of the comparative examples although the former ointments developed some bleeding at 45° C.

TABLE 1

| Irritation Test of Bases | |
|---|---|
| Sample | Percent positive |
| Example 1 | 0/60 |
| Example 2 | 0/60 |
| Example 3 | 1/60 |
| Comparative Example 1 | 0/60 |
| Comparative Example 2 | 2/60 |
| Comparative Example 3 | 2/60 |
| Comparative Example 4 | 7/60 |
| Comparative Example 5 | 4/60 |

TABLE 2

| | Physicochemical Stability (Observation after 6 Months) | | | | | | | | |
|---|---|---|---|---|---|---|---|---|---|
| | Discoloration* | | | Bleeding** | | | Content, % | | |
| | Storage conditions | | | | | | | | |
| Item observed Sample | Room temp. | 45° C. | 1000 lux | Room temp. | 45° C. | 1000 lux | Room temp. | 45° C. | 1000 lux |
| Example 1 | — | — | — | — | ± | — | 100.2 | 99.8 | 99.7 |
| Example 2 | — | — | — | — | ± | — | 99.6 | 99.4 | 98.6 |
| Example 3 | — | — | — | — | ± | — | 100.6 | 100.2 | 100.1 |
| Comparative Example 1 | — | — | ± | — | — | — | 101.1 | 98.8 | 99.6 |
| Comparative Example 2 | — | — | — | — | ± | — | 99.7 | 98.8 | 94.0 |
| Comparative Example 3 | — | — | — | ± | + | ± | 100.5 | 99.7 | 93.3 |
| Comparative Example 4 | — | ± | ± | / | / | / | 100.9 | 88.7 | 85.1 |
| Comparative Example 5 | — | ± | ± | / | / | / | 101.6 | 94.8 | 95.5 |

*Discoloration: — no discoloration. ± some discoloration. + aparent discoloration.
**Bleeding: — no bleeding. ± some bleeding. + rather substantial bleeding.

What is claimed is:

1. An anhydrous ointment consisting essentially of the following ingredients (a) and (b):
   (a) 0.05–1 wt % of deprodone propionate; and
   (b) 89–99.95 wt % of a base formed of white petrolatum and a liquid hydrocarbon,
   wherein the white petrolatum is present in an amount of 74–98.95 wt % of (b), and the liquid hydrocarbon is present in an amount of 1–15 wt % of (b).

2. The ointment of claim 1, further containing
   (c) 1–10 wt. % of a polyhydric alcohol.

3. The ointment of claim 1, further containing a stabilizer.

4. The ointment of claim 2, further containing a stabilizer.

5. The ointment of claim 2, wherein the polyhydric alcohol ingredient (c) is glycerin, sorbitol, sorbitan or a glycol.

6. The ointment of claim 3, wherein the stabilizer is butylhydroxyanisole or dibutylhydroxytoluene.

7. The ointment of claim 4, wherein the polyhydric alcohol ingredient (c) is glycerin, sorbitol, sorbitan or a glycol.

8. The ointment of claim 4, wherein the stabilizer is butylhydroxyanisole or dibutylhydroxytoluene.

9. The ointment of claim 7, wherein the stabilizer is butylhydroxyanisole or dibutylhydroxytoluene.

* * * * *